United States Patent [19]

Ichikawa et al.

[11] 4,127,464
[45] Nov. 28, 1978

[54] SENSOR FOR DETECTING OXYGEN CONCENTRATION

[75] Inventors: Norio Ichikawa, Mito; Sadayasu Ueno, Katsuta, both of Japan

[73] Assignee: Hitachi, Ltd., Tokyo, Japan

[21] Appl. No.: 756,714

[22] Filed: Jan. 4, 1977

[30] Foreign Application Priority Data

Jan. 23, 1976 [JP] Japan .................................. 51-6900

[51] Int. Cl.² .............................................. G01N 27/46
[52] U.S. Cl. ................................................... 204/195 S
[58] Field of Search ............................... 204/15, 195 S

[56] References Cited

U.S. PATENT DOCUMENTS

| | | | |
|---|---|---|---|
| 3,616,407 | 10/1971 | Engell et al. | 204/195 S |
| 3,619,381 | 11/1971 | Fitterer | 204/195 S |
| 3,791,954 | 2/1974 | Noda et al. | 204/1 S |
| 3,841,987 | 10/1974 | Friese et al. | 204/195 S |
| 3,844,920 | 10/1974 | Burgett et al. | 204/1 S |
| 3,960,693 | 6/1976 | Weyl et al. | 204/195 S |
| 4,007,106 | 2/1977 | Hone et al. | 204/195 S |
| 4,019,974 | 4/1977 | Weyl et al. | 204/195 S |

FOREIGN PATENT DOCUMENTS 2,326,086 12/1974 Fed. Rep. of Germany ....... 204/195 S Primary Examiner—T. Tung
Attorney, Agent, or Firm—Craig and Antonelli

[57] ABSTRACT

A sensor is provided for electrochemically detecting the oxygen concentration of exhaust gas from an internal combustion engine of a vehicle. The sensor has an oxygen ion-transferrable solid electrolyte partition wall having catalyst electrodes on both sides in its housing, to thereby separate the housing into a reference gas contact compartment and an exhaust gas contact compartment in a hermetically isolated state between the two compartments. The reference gas contact compartment is sealed off from the surrounding atmosphere, but communicates with the atmosphere at a desired location in the vehicle only through an extended passage for introducing air as the reference gas into the reference gas contact compartment. The solid electrolyte partition wall is protected from splashing of water droplets, and consequently from quenching, ensuring an increased durability or life of the sensor without damage.

5 Claims, 2 Drawing Figures

SENSOR FOR DETECTING OXYGEN CONCENTRATION

This invention relates to a sensor for electrochemically detecting an oxygen concentration of exhaust gas evolving, for example, from an internal combustion engine, and more particularly to a sensor for detecting an oxygen concentration by feeding a reference gas to one side of an oxygen ion-transferrable solid electrolyte partition wall having electrodes on both its sides, and feeding an exhaust gas, whose oxygen concentration is to be measured, to the other side of the solid electrolyte partition wall, and measuring the difference in electrical potential generated between these two electrodes.

To facilitate understanding of the structure and problems of the prior art as well as the structure and advantages of the present invention, reference is made to the description below and to the accompanying drawings.

Figure 1:
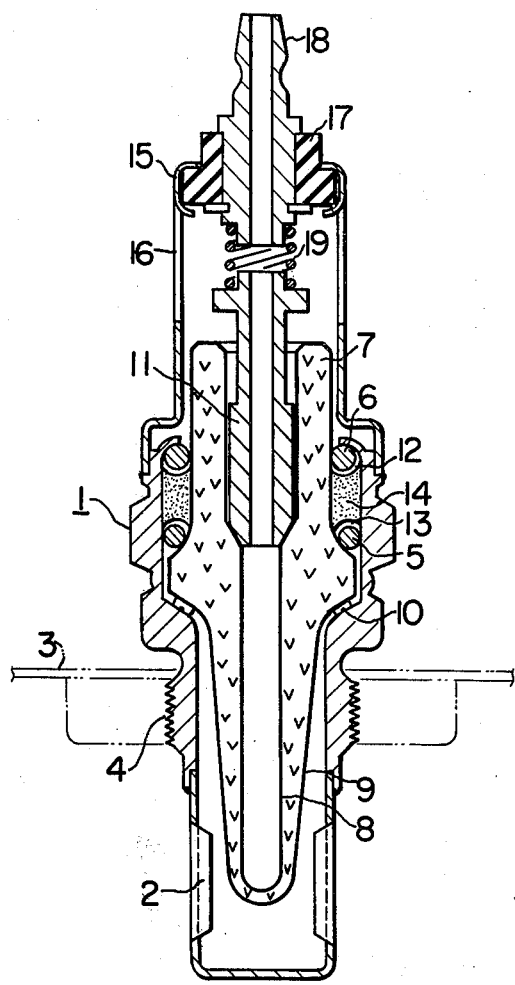
FIG. 1 is a cross-sectional view of a prior art sensor for detecting oxygen concentration.

In FIG. 1 is shown the structure of the prior art sensor usually used for detecting oxygen concentration of exhaust gas evolving, for example, from automobiles (Laid-Open Japanese Patent Application No. 1285/74). Housing 1 has an inlet 2 for introducing an exhaust gas whose oxygen concentration is to be measured, and also has, on its definite circumferential position, a screw part 4 to be engaged with a support 3 on the exhaust pipe, etc. of an automobile to fix the housing 1. In the housing 1, an oxygen ion-transferrable solid electrolyte partition wall 7 in any form, usually in a form of hollow cylinder having one closed end as shown in the drawing, is hermetically provided and fixed by a fixing ring 5 and a caulking ring 6, thereby separating the housing 1 into an exhaust gas contact compartment and a reference gas contact compartment in a hermetically isolated state between the two compartments. Electrodes comprising noble metal such as platinum, etc. are provided on both side of the solid electrolyte partition wall 7 by vapor deposition, etc., thereby forming an electrode 9 on the side of the exhaust gas contact compartment, and an electrode 8 on the side of the reference gas contact compartment, respectively. The electrode 9 on the side of the exhaust gas contact compartment is electrically connected to the housing 1 through a chip 10, whereas the electrode 8 on the side of the reference gas contact compartment abuts on a cylindrical metallic bush 11, and is electrically connected with the bush 11. Upper end of the housing 1 is caulked over the outer periphery of the caulking ring 6 to support the solid electrolyte partition wall 7 and also keep in a hermetic state a space between the caulking ring 6 and the fixing ring 5 by means of an upper washer 12, a lower washer 13, and a heat-resistant, air-tight seal 14 comprising asbestos, etc. A cover 15 is fixed by welding at an upper end of the housing to enclose the part of the solid electrolyte partition wall 7 projected from the upper end of the housing 1. The cover 15 has an opening 16 for introducing air as the reference gas, and also has an insulating tube 17 comprised, for example, of fluorine resin, etc.

A terminal 18 of hollow electrical conductor is fixed inside the insulating tube 17, and a compressible coil spring 19 is provided between the terminal 18 and the metallic bush 11, and also electrically communicates the metallic bush 11 with the terminal 18. Furthermore, the spring 19 ensures the contact of the electrode 8 at the side of the reference gas contact chamber with the metallic bush 11. In such a structure, air as the reference gas is introduced through the opening 16 in the cover 15 into the reference gas contact compartment to contact the electrode 8 on the side of the reference gas contact compartment, whereas exhaust gas, whose oxygen concentration is to be measured, is introduced through the opening 2 in the housing 1 into the exhaust gas contact compartment to contact the electrode 9 at the side of the exhaust gas contact compartment, whereby a difference in potential is generated between the electrodes 8 and 9. The difference in potential is taken out as difference in potential between the housing 1 and the terminal 18, whereby the oxygen concentration of the exhaust gas can be detected.

However, since the air as the reference gas is introduced through the opening 16, which is open near the solid electrolyte partition wall 7, in the prior art sensor for detecting the oxygen concentration, there is a fear of splashing of water droplets such as those of rain water, mud water, sea water, etc. onto the ceramic solid electrolyte partition wall 7 heated to about 700° to 800° C. through said opening 16, when the sensor for detecting the oxygen concentration is fixed to an exhaust gas pipe under the chassis of vehicle. As a result, the solid electrolyte partition wall 7 is quenched in that case, thereby developing cracks thereon, and damaging the sensor.

An object of the present invention is to provide a sensor for detecting the oxygen concentration of exhaust gas with a long life by preventing water invasion from the opening for introducing the reference gas, thereby protecting the solid electrolyte partition wall.

According to the present invention, said object can be attained by hermetically sealing the reference gas contact compartment of the housing, and providing in the reference gas contact compartment an extended passage communicating with the atmosphere at one end and the reference gas contact compartment at other end, thereby introducing the reference gas into the reference gas contact compartment from a desirable position.

That is, the present invention provides a sensor for detecting an oxygen concentration in exhaust gas, which comprises:

(i) a housing,
(ii) an oxygen ion-transferrable solid electrolyte partition wall hermetically provided in the housing, thereby partitioning the housing into an exhaust gas contact compartment and a reference gas contact compartment,
(iii) catalyst electrodes provided on both sides of the solid electrolyte partition wall as an electrode on the side of the exhaust gas contact compartment and an electrode on the side of the reference gas contact compartment,
(iv) electrical conductors electrically connected to the respective catalyst electrodes, thereby transmitting a difference in potential between the catalyst electrodes to outside the housing,
(v) an inlet opening for exhaust gas provided in the exhaust gas contact compartment of the housing, and
(vi) an extended passage for reference gas, whose one end is open to atmosphere and whose other end is open to the hermetic reference gas contact chamber of the housing.

According to one embodiment of the present invention, the extended passage can be a pipe, which may be integrated at its outside with the electrical conductor electrically connected to the electrode on the side of the reference gas contact compartment of the housing.

According to another embodiment of the present invention, the extended passage may be integrated with the electrical conductor electrically connected to the electrode on the side of the reference gas contact compartment of the housing, or the resulting extended passage integrated with the electrical conductor may be a stranded conductor with a core at its inside and with a water-proof insulation jacket at its outside, or the stranded conductor may be of stainless steel or copper, and the core may be fishing net yarns, or the resulting extended passage integrated with the electrical conductor may be stranded stainless steel wires with a water-proof insulation jacket at its outside.

According to other embodiments of the present invention, the extended passage may be integrated with the electrical conductor electrically connected to the catalyst electrode on the side of the reference gas contact compartment of the housing; a water-proof insulation jacket may be provided on the outside of the extended passage integrated with the electrical conductor; a guide bush of electro-conductive material, which is electrically connected to the catalyst electrode on the side of the exhaust gas contact compartment of the housing and hermetically seals the reference gas contact compartment of the housing, may be provided on the outside of the water-proof insulation jacket; a metallic braided armour wire may be provided on the outside of the guide bush, the metallic braided armour wire being fixed to the guide bush by means of a cap provided on the outside of the metallic braided armour wire, or the extended passage integrated with the electrical conductor may be a stranded conductor with a core at its inside, or the stranded conductor may be of stainless steel or copper, and the core may be fishing net yarns, or the extended passage integrated with the electrical conductor may be of stranded stainless steel wires.

Figure 2:
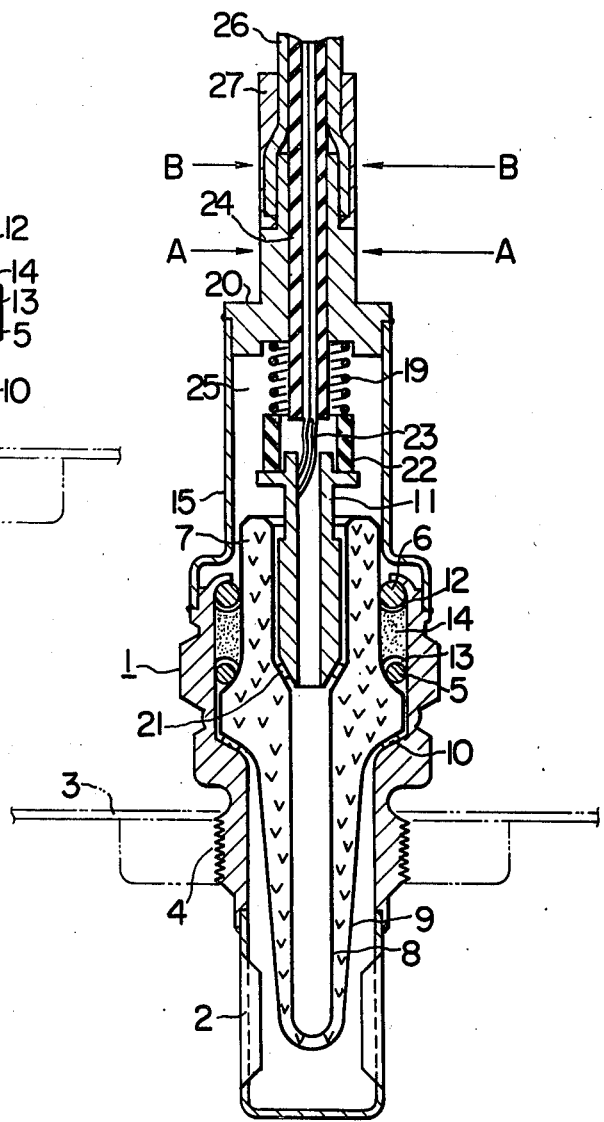
FIG. 2 is a cross-sectional view of one embodiment of a sensor for detecting oxygen concentration in accordance with the present invention.

The present invention will be described below in detail, referring to one embodiment illustrated in FIG. 2, wherein identical constituent parts with those of the prior art illustrated in FIG. 1 are indicated with the identical numerals from brevity of description.

Housing 1 is fixed to a support on an exhaust gas pipe, etc. by means of screw 4, so that an opening 2 for introducing exhaust gas can be in the exhaust gas pipe. In the housing 1, an oxygen ion-transferring solid electrolyte partition wall 7 having a catalyst electrode 8 on the side of reference gas contact compartment and a catalyst electrode 9 on the side of exhaust gas contact compartment is hermetically fixed by a fixing ring 5, a caulking ring 6, a chip 10, an upper washer 12, a lower washer 13, and a seal 14, thereby separating the housing into a reference gas contact compartment and an exhaust gas contact compartment in a hermetically isolated state between the two compartments.

A cover 15 free from any opening is hermetically fixed by welding at the upper end of the housing 1 at the entire periphery, so that the cover 15 can enclose the part projected from the upper end of the housing 1, and furthermore a guide bush 20 of electrical conductor is fixed by welding to the upper end of the cover 15 at its entire periphery.

A cylindrical metallic bush 11 abuts on the electrode 8 on the side of reference gas contact compartment through a tip 21, and a compressible coil spring 19 is provided between insulating ring 22 placed on the upper face of the metallic bush 11 and made of steatite, etc., and the guide bush 20. The spring 19 ensures electrical connection of the metallic bush 11 to the electrode 8 on the side of reference gas contact compartment.

An electrical conductor 23 of core-wires, for example, made of fishing net yarns as core, provided with stranded stainless steel wires around the core, extends through the center of guide bush 20. One end of the electrical conductor 23 of core-wires is fixed to the inner wall of the hollow part of the metallic bush 11, whereas other end thereof is connected to the desired location, for example, a point for receiving the detected voltage within the vehicle (not shown in the drawing). The electrical conductor 23 of core-wires is coated at its outer surface with an insulating jacket 24 of insulating material such as silicone rubber, fluorine resin, etc. To prevent water invasion from any clearance formed between the insulating jacket 24 and the guide bush 20, the entire outer surface of the guide bush 20 is mechanically caulked in the direction of arrow marks A, whereby a housing compartment 25 formed at the side of the reference gas contact compartment of the housing 1 is hermetically sealed off from the surrounding atmosphere around the housing 1. The housing compartment 25 communicates with the atmosphere at the desired location in the vehicle through clearances in the electrical conductor 23 of core-wires, and the air as the reference gas can be introduced through the clearances into the housing compartment 25. The air as the reference gas spontaneously flows in or out of the housing compartment 25, through the clearances by aspirating action of the housing 1 due to a temperature change, and expansion and contraction of air in the reference gas contact compartment, caused by temperature changes in the exhaust gas pipe, or further by diffusing action of the air.

The upper part of the guide bush 20 has a smaller outer diameter, and is jacketed with an armored electrical conductor 26 of metallic braided armour wire such as braided stainless steel wires, etc., which is also provided on the outer surface of the insulating jacket 24 extended from the upper end of the guide bush 20. The armored electrical conductor 26 is also fixed by welding to the guide bush 20. The jacketing part of the armored electrical conductor 26 is fixed by caulking in the direction of arrow marks B together with a cylindrical cap 27 inserted around the armored electrical conductor 26, thereby protecting the welded part of conductor 26, and fixing the latter. The other end of conductor 26 is electrically connected to the point for receiving the detected potential.

To detect the oxygen concentration of exhaust gas in such a structure of the present sensor as described above, the reference gas is introduced into the housing compartment 25 through the clearances of the electrical conductor 23 of core-wires from the point for receiving the detected potential in the vehicle, and at the same time an exhaust gas, whose oxygen concentration is to be measured, is introduced into the exhaust gas contact compartment of the housing 1 through the opening 2. Then, a difference in potential is generated between the electrodes 8 and 9 on both sides of the solid electrolyte partition wall 7, and is detected through the electrical conductor 23 of core-wires, and the armored electrical conductor 26.

According to the present embodiment as described above, the housing compartment 25 at the reference gas contact side is sealed off from the surrounding atmosphere, and the air as the reference gas is introduced into the housing compartment 25 through the clearances of the electrical conductor 23 of core-wires. That is, water droplets such as those of rain water, etc. are not splashed onto the solid electrolyte partition wall 7 at an elevated temperature, and therefore cracks, etc. due to quenching are never developed.

When the electrical conductor 23 of core-wires is comprised only of stranded wires of stainless steel or copper, its resistance to vibration is not only improved, but also the air as the reference gas can be introduced without using any core or tube. When the armored electrical conductor 26 is connected to the outermost periphery of the guide bush 20, an invasion of water to the inside of the guide bush 20 due to a capillary action of the braided structure of the armour can be prevented. By caulking the connection part of the armour electrical conductor 26 of metallic braided armour wires together with the cap 27, a complete protection of the connection part can be made.

In the present embodiment as described above, the extended passage for the reference gas, which connects the housing compartment 25 to the desired location with no danger of water splashing in a vehicle, is comprised of the integrated electrical conductor of core-wires 23, but an independent passage such as a tube can be used, or an electrical conductor 23 having a tube as the core or an electrical conductor 23 of core-wires jacketed with an insulating jacket 24 having a tubular passage between the conductor and the jacket can be used as the integrated extended passage for introducing the reference gas. In brief, any passage can be used, so long as the passage can introduce the air as the reference gas from the desired location having no fear of water splashing in a vehicle to the housing compartment 25 sealed off from the surrounding atmosphere. However, in that case, the introduction of the reference gas through an extended passage in the form of an electrical conductor of core-wires as 23 is more advantageous in reduction of the number of the necessary parts than that in the form of an independent tube, and an extended passage in the form of only stranded wires of stainless steel or copper is much more advantageous in improving the resistance to vibration.

In the present invention, the reference gas contact compartment of the housing for a sensor for detecting an oxygen concentration of exhaust gas is sealed off from the surrounding atmosphere, and the reference gas contact compartment communicates with the desired location for introducing the reference gas in a vehicle through an extended passage, and consequently damaging of the solid electrolyte partition wall due to splashing of water droplets and consequent quenching can be prevented, thereby considerably increasing the durability or life of the sensor.

What is claimed is:

1. A sensor for detecting an oxygen concentration in exhaust gas, which comprises:
   (i) a housing,
   (ii) an oxygen ion-transferable solid electrolyte partition wall hermetically provided in the housing, thereby partitioning the housing into an exhaust gas contact compartment and a reference gas contact compartment,
   (iii) catalyst electrodes provided on both sides of the solid electrolyte partition wall, one of said electrodes constituting an electrode on the side of the exhaust gas contact compartment and another of said electrodes constituting an electrode on the side of the reference gas contact compartment,
   (iv) electrical conductors electrically connected to the respective catalyst electrodes for transmitting a difference in potential between the catalyst electrodes to the exterior of the housing,
   (v) an inlet opening for exhaust gas provided in the exhaust gas contact compartment of the housing, and
   (vi) an extended passage for reference gas, said passage having one end open to atmosphere and having the other end open to the reference gas contact compartment of the housing, said extended passage being formed by the electrical conductor connected to the electrode in the reference gas contact compartment and a waterproof insulation jacket surrounding said electrical conductor, said electrical conductor being a stranded conductor having a core at its inside.

2. A sensor for detecting oxygen concentration in exhaust gas, which comprises:
   (i) a housing;
   (ii) an oxygen ion-transferable solid electrolyte partition wall hermetically provided in the housing, thereby partitioning the housing into an exhaust gas contact compartment and a reference gas contact compartment;
   (iii) catalyst electrodes provided on both sides of the solid electrolyte partition wall constituting an electrode on the side of the exhaust gas contact compartment and an electrode on the side of the reference gas contact compartment;
   (iv) electrical conductors electrically connected to the respective catalyst electrodes for transmitting a difference in potential between the catalyst electrodes to the exterior of the housing;
   (v) an inlet opening for exhaust gas provided in the exhaust gas contact compartment of the housing;
   (vi) a waterproof insulation jacket around the conductor connected to the electrode on the side of the reference gas contact compartment, said jacket defining an extended passage having one end open to the atmosphere and having the other end open to the reference gas contact compartment of the housing for introducing reference gas into said reference gas contact compartment;
   (vii) a guide bush of electroconductive material on the outside of said water-proof insulation jacket, said guide bush being electrically connected to the catalyst electrode on the side of the exhaust gas contact compartment of the housing and forming a hermetic seal with the reference gas contact compartment of the housing;
   (viii) a metallic braided armor wire on the outside of said guide bush; and
   (ix) cap means on the outside of said metallic braided armor wire for securing said metallic braided armor wire to said guide bush.

3. A sensor according to claim 2, wherein the the electrical conductor includes a stranded conductor with a core at its inside.

4. A sensor according to claim 3, wherein said stranded conductor is of stainless steel or copper, and the core is fishing net yarns.

5. A sensor according to claim 2, wherein the electrical conductor includes stranded stainless steel wires.

* * * * *